(12) United States Patent
Cooper

(10) Patent No.: US 10,307,435 B2
(45) Date of Patent: Jun. 4, 2019

(54) EXERCISE PERFORMANCE ENHANCERS

(71) Applicant: University of Georgia Research Foundation, Inc., Athens, GA (US)

(72) Inventor: Jamie A. Cooper, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 48 days.

(21) Appl. No.: 15/381,877

(22) Filed: Dec. 16, 2016

(65) Prior Publication Data

US 2017/0173061 A1 Jun. 22, 2017

Related U.S. Application Data

(60) Provisional application No. 62/268,365, filed on Dec. 16, 2015.

(51) Int. Cl.
| | | |
|---|---|---|
| *A61K 31/7016* | (2006.01) | |
| *A61K 47/30* | (2006.01) | |
| *A61K 9/00* | (2006.01) | |
| *A61K 9/08* | (2006.01) | |
| *A61K 9/70* | (2006.01) | |
| *A23L 33/125* | (2016.01) | |

(52) U.S. Cl.
CPC ........ *A61K 31/7016* (2013.01); *A23L 33/125* (2016.08); *A61K 9/006* (2013.01); *A61K 9/7007* (2013.01); *A61K 9/0056* (2013.01)

(58) Field of Classification Search
CPC ...... A61K 31/7016; A61K 47/30; A61K 9/08; A61K 9/7007; A61K 9/006; A23L 33/125; A23V 2002/00
USPC .......................................................... 514/23
See application file for complete search history.

(56) References Cited

U.S. PATENT DOCUMENTS

2014/0335153 A1* 11/2014 Allen ................... A61K 9/006
424/450

OTHER PUBLICATIONS

Andersen et al. Effect of Oral Sucrose Shortly Before Exercise on Work Capacity in McArdle Disease. Arch Neurol. 2008;65(6):786-789. (Year: 2008).*
Fares et al. CarbohydrateMouth Rinse Effects on Exercise Capacity in Pre- and Postprandial States. Journal of Nutrition and Metabolism vol. 2011, Article ID 385962, 6 pages. doi:10.1155/2011/385962. Jul. 20, 2011. (Year: 2011).*
Bartoshuk LM, Duffy VB, Hayes JE, Moskowitz HR, Snyder DJ. Psychophysics of sweet and fat perception in obesity: problems, solutions and new perspectives. Philos Trans R Soc Lond B Biol Sci. Jul. 29, 2006; 361:1137-48.
Berthoud HR. Brain, appetite and obesity. Physiol Behav. May 19, 2005; 85:1-2.
Berthoud HR. Homeostatic and non-homeostatic pathways involved in the control of food intake and energy balance. Obesity (Silver Spring). Aug. 2006; 14 Suppl 5:197S-200S.
Berthoud HR. Interactions between the "cognitive" and "metabolic" brain in the control of food intake. Physiol Behav. Aug. 15, 2007; 91:486-98.
Berthoud HR. Metabolic and hedonic drives in the neural control of appetite: who is the boss? Curr Opin Neurobiol. Dec. 2011; 21:888-96.
Berthoud HR. Neural control of appetite: cross-talk between homeostatic and non-homeostatic systems. Appetite. Dec. 2004; 43:315-7.
Carter JM, Jeukendrup AE, Jones DA. The effect of carbohydrate mouth rinse on 1-h cycle time trial performance. Med Sci Sports Exerc. Dec. 2004; 36:2107-11.
Connolly L, Coveleskie K, Kilpatrick LA, Labus JS, Ebrat B, Stains J, Jiang Z, Tillisch K, Raybould HE, Mayer EA. Differences in brain responses between lean and obese women to a sweetened drink. Neurogastroenterol Motil. 2013; 25:579-e460.
Drewnowski A, Mennella JA, Johnson SL, Bellisle F. Sweetness and food preference. J Nutr. Jun. 2012; 142:1142S-8S.
Frank GK, Oberndorfer TA, Simmons AN, Paulus MP, Fudge JL, Yang TT, Kaye WH. Sucrose activates human taste pathways differently from artificial sweetener. Neuroimage. Feb. 15, 2008; 39:1559-69.
Henquin JC. Do pancreatic beta cells "taste" nutrients to secrete insulin? Sci Signal. Aug. 28, 2012; 5:e36K.
Kojima I, Nakagawa Y. The Role of the Sweet Taste Receptor in Enteroendocrine Cells and Pancreatic beta-Cells. Diabetes Metab J. Oct. 2011; 35:451-7.
LeBlanc J. Nutritional implications of cephalic phase thermogenic responses. Appetite. Apr. 2000; 34:214-6.
Lenard NR, Berthoud HR. Central and peripheral regulation of food intake and physical activity: pathways and genes. Obesity (Silver Spring). Dec. 2008; 16 Suppl 3:S11-S22.
McCaughey SA. The taste of sugars. Neurosci Biobehav Rev. Jul. 2008;32:1024-43.
Parra-Covarrubias A, Rivera-Rodriguez I, Almaraz-Ugalde A. Cephalic phase of insulin secretion in obese adolescents. Diabetes. Dec. 1971; 20:800-2.
Pottier A, Bouckaert J, Gilis W, Roels T, Derave W. Mouth rinse but not ingestion of a carbohydrate solution improves 1-h cycle time trial performance. Scand J Med Sci Sports. Feb. 2010; 20:105-11.
Shin AC, Zheng H, Berthoud HR. An expanded view of energy homeostasis: neural integration of metabolic, cognitive, and emotional drives to eat. Physiol Behav. Jul. 14, 2009;97:572-80.
Small DM. Taste representation in the human insula. Brain Struct Funct. Jun. 2010; 214:551-61.
Teff K. Nutritional implications of the cephalic-phase reflexes: endocrine responses. Appetite. Apr. 2000; 34:206-13.
Yang Q. Gain weight by "going diet?" Artificial sweeteners and the neurobiology of sugar cravings: Neuroscience 2010. Yale J Biol Med. Jun. 2010;83:101-8.

(Continued)

*Primary Examiner* — Yih-Horng Shiao
(74) *Attorney, Agent, or Firm* — Meunier Carlin & Curfman LLC

(57) ABSTRACT

Disclosed are compositions, articles, and method for enhancing exercise performance in a subject. The method involves contacting the oral cavity of the subject with a composition comprising a sweet and caloric food product for a period sufficient to cause a cephalic phase response in the subject.

9 Claims, 3 Drawing Sheets

(56) References Cited

OTHER PUBLICATIONS

Zheng H, Berthoud HR. Neural systems controlling the drive to eat: mind versus metabolism. Physiology (Bethesda). Apr. 2008; 23:75-83.

* cited by examiner

EXERCISE PERFORMANCE ENHANCERS

CROSS-REFERENCE TO RELATED APPLICATIONS

This application claims benefit of U.S. Provisional Application No. 62/268,365, filed Dec. 16, 2015, which is hereby incorporated herein by reference in its entirety.

BACKGROUND

Discovering ways to delay fatigue during exercise has long been a strategy for endurance athletes to enhance performance. Most of the focus remains on peripheral fatigue development in muscle fibers due to limits in oxygen transport or metabolic capacity within the muscle. However, fatigue specifically related to motor unit activity, which is controlled by the central nervous system (CNS), is gaining recognition.

SUMMARY

Disclosed are compositions, articles, and method for enhancing exercise performance in a subject. The method involves contacting the oral cavity of the subject with a composition comprising a sweet and caloric food product for a period sufficient to cause a cephalic phase response in the subject. In some cases, this occurs without substantial ingestion of the food product. Cephalic phase responses (CPRs) are innate and learned physiological responses to sensory signals that prepare the gastrointestinal tract for the optimal processing of ingested foods. Since the CPRs will diminish, even if the sweet taste continues, contact with the oral cavity is not continuous. In some embodiments, the period is 5 to 30 seconds, 5 to 45 seconds, 5 to 60 seconds, or 5 to 90 seconds. However, CPRs can be caused again after a fasting period. Therefore, in some embodiments, the oral cavity of the subject is contacted again with the composition after fasting intervals of at least 6 to 10 minutes. For endurance exercises that last more than 60 minutes, athletes should ingest food to restore energy. Moreover, the benefits of CPRs may diminish over time. Therefore, in some cases, the oral cavity is contacted with the composition during the last 20 to 40 minutes of the exercise.

As disclosed herein, the food product preferably both contains energy (calories) and is sweet to the taste in order to cause a CPR. In some cases, the food product comprises a sugar, such as sucrose. Sweetness is commonly measured by comparison to reference solutions of sucrose. Therefore, in some cases, the food product is present in an amount equivalent to at least 3%, 4%, 5%, 6%, 7%, 8%, 9%, or 10% sucrose.

The composition can be in any dosage form that maximizes buccal administration and minimizes ingestion. In some cases, the composition is a tablet, capsule, lozenge, film, or strip that can completely dissolve in the oral cavity of a human subject within 10, 20, 25, 30, 35, 40, 45, 50, or 60 seconds. In some embodiments, the composition is a rapidly dissolving orally consumable film or strip. For example, the film or strip can comprises a mucoadhesive polymer.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
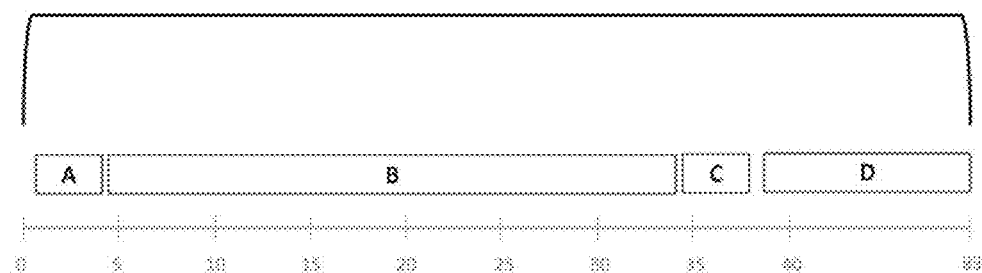
FIG. 1 depicts sequence of events during fMRI (displayed in seconds). (A) administering solution (3 sec), (B) hold solution in the mouth (30 sec), (C) Swallow solution (3 sec), (D) Q1-5: subjective ratings based on sweetness, bitterness, saltiness, palatability, and intensity of each solution (7 s displaying question, 2 s between questions).

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sweet" and "sweetness" is commonly measured by comparison to reference solutions of sucrose. Sucrose is the standard to which all other sweeteners are compared. Humans can recognize sweetness in about 1 or 2% sucrose solution. Coffee is typically sweetened to about the level of 5% sucrose. Soft drinks are usually about as sweet as 10% sucrose. 15% sucrose is really sweet and starts to feel a little syrupy. Other sweeteners are then tasted at a series of dilutions to determine the concentration that is as sweet as a given percent sucrose reference. For a detailed discussion, see "A Systematic Study of Concentration-Response Relationships of Sweeteners," G. E. DuBois, et al, in Sweeteners: Discovery, Molecular Design and Chemoreception, D. E. Walters, et al., Eds., American Chemical Society, Washington, D.C. (1991), pp 261-276, which is incorporated herein by reference for the teaching of methods for determining sweetness.

The term "sugar" refers to sweet, short-chain, soluble carbohydrates. As used herein, the term refers only to edible carbohydrates that contain calories. Examples include glucose, sucrose, fructose, and sucrose.

Sweet sugars can be from natural and synthetic sources and includes brown sugars, granulated sugars, syrups, milled sugars, molasses, and polyols (sugar alcohols). In some cases, the sugar comprises corn syrup, high fructose corn syrup, honey, maple syrup, molasses, brown rice syrup, beet sugar, or cane sugar.

The disclosed compositions may be formulated as a solid or semi-solid. Solid and semi-solid formulations refer to any formulation other than aqueous formulations. Examples include a gel, a lozenge, a gum, a gel strip or film.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Effect of Sweetened Mouth Rinses on Resting and Exercise Measures

A strategy for reducing central fatigue is to rinse the oral cavity with a carbohydrate (CHO) solution while exercising to possibly stimulate reward related areas in the brain involved in improving motor control during exercise as part of a central response in the brain in order to enhance endurance performance. Using functional magnetic resonance imaging (fMRI), it was shown that oral exposure to glucose and maltodextrin (MALT) activated reward-related brain regions which were unresponsive to saccharin alone, suggesting that the enhancement of exercise performance was due to activation of glucose receptors in the mouth that were mediating an increase in central drive mechanisms. As disclosed herein, sweet taste, which is associated with increased neural activation in reward related areas of the brain, is also contributing to the overall ergogenic effect of a sweetened mouth rinse.

Sweet taste perception can trigger the brain reward system for measures of taste quality as well as an incentive motivational component (McCaughey S A. Neurosci Biobehav Rev. 2008 32:1024-43). However, no prior studies have isolated the effects of sweet taste, independent of energy availability, as it relates to mouth rinsing a solution as an ergogenic aid during exercise. Therefore, experiments were conducted to examine the ergogenic effects of sweet taste, the intensity of sweet taste, and energy (kcal) content from different mouth rinses on exercise performance during a 12.8 km time trial. To study sweet taste, intensity, and energy, four different solutions were employed: water (unsweetened control), two sucralose solutions with differing sweetness intensities (but no energy since it is an artificial sweetener), and sucrose which contains energy and has a sweet taste. It was hypothesized that exercise performance would be enhanced more by using a mouth rinse containing sucrose than either sucralose solution due to the availability of energy and sweet taste, and also that the three sweetened mouth rinses will provide an increased ergogenic effect compared to water. It was also hypothesize that the higher intensity sucralose solution would improve time trial performance over the lower intensity sucralose solution. Finally, fMRI was used to examine the hemodynamic response associated with each solution utilized in the exercise protocol Methods Design This study was a randomized, single blind crossover design that took place in the Human Nutrition Lab (HNL) and the indoor track at Texas Tech University. All subjects (n=24; NS:14, OB:10) completed four (4) study visits separated by at least 4 days, and each visit took place at the same time of day (between 0600-0900 hours). For visit 1-4, subjects performed a 12.8 km running time trial with the only difference between trials being the different mouth rinse solution being administered at each visit in a random order. Seventeen of the same subjects (NW: 7, OB: 10). For visit 5, subjects reported to the Texas Tech University Neuroimaging Center for an fMRI scan to examine brain areas associated with exposure to each solution. All procedures were approved by the Institutional Review Board at Texas Tech University and written informed consent was obtained from each subject prior to starting study procedures.

Subjects

Twelve (12) male and nine (9) female trained endurance athletes were recruited for participation in the study. Inclusion criteria for participation was that individuals must train in aerobic exercise at least 4 days per week for at least 1 hour per day, between the ages of 18-45, and a BMI between 18.5-24.9 kg/m2. Exclusion criteria for the study included changes in current exercise program, a low carbohydrate diet, chronic diseases or medications that could alter metabolic rate or hydration statues, nicotine use, pregnancy or nursing. Individuals were also excluded if they had a sensitivity or allergy to red food dye FD&C Red No. 40 or sucralose. Women were tested only during the follicular phase of their menstrual cycle (days 3-9) to control for any fluctuation in hormones. Subjects were asked to arrive for each visit following an 8-12 hour fast with no vigorous exercise for 12 hours before, and they were asked to not brush their teeth with toothpaste before arriving.

Mouth Rinse Solutions

The four treatments or mouth rinse solutions that were used in a random order were: (1) a sucrose solution (S), (2) a sucralose solution that has a 1:1 ratio of sweetness intensity with sucrose (S1:1), (3) a sucralose solution that is 100:1 ratio of sweetness intensity with sucrose (S100:1), and (4) a water solution (25 mL of water as a control) (C). The S solution will consist of 64 g of sucrose dissolved in 1000 mL of water, with a bolus of 25 mL being used for the mouthwash protocol. The S100:1 solution will consist of 10.5 g of sucralose powder (American Health Foods and Ingredients, CA) dissolved in 1000 mL of water, with a bolus of 25 mL being used for the mouthwash protocol. This amount of sucralose will make the mouth rinse 100 times as sweet as sucrose to investigate the effects of sweetness intensity. The S1:1 solution will consist of 0.11 g of sucralose powder dissolved in 1000 ml of water, with a bolus of 25 mL being used for the mouthwash protocol. This amount of sucralose makes the solution have a 1:1 sweetness with sucrose. The concentrations of each solution were determined based on manufacturer recommendations and psychophysical information collected from a panel of subjects. Each mouth rinse solution will have 2 mL of red food dye FD&C Red No. 40 to ensure the same sensory response through appearance.

Protocol

Baseline Testing (Visit 1):

Following an overnight fast, participants reported to the HNL for baseline testing. Height, body weight, body composition, and blood pressure measurements were taken. Body composition measures were done using air displacement plethysmography with the BodPod (Cosmed USA, Inc Concord, Calif.). Participants then answered questions regarding their current and usual exercise patterns. These questions were used to document the type, frequency, duration, and intensity of exercise.

Exercise Interventions (Visits 1-4):

Following baseline testing participants reported to the indoor track at Texas Tech University to complete a 12.8 km running time trial. Participants were asked to consume a standard diet (55-60% carbohydrates, 15-20% protein, and 20-25% fat) and keep a dietary log for 24 hours prior to the first visit. They were also asked not to consume alcohol or caffeine during this period. The evening meal consumed prior to visit 1 was repeated exactly before each subsequent visit. Subjects were asked to keep a training log for 7 days prior to each visit. The participants will then be asked to follow the same training as what was reported on their training log between study visits.

For the time trial, subjects were fitted with a heart rate (HR) monitor. The only instruction the subjects were given was related to the distance of the time trial and that they should try to complete the 12.8 km time trail as quickly as possible. Each subject was given 10 minutes to warm up before the time trial begins. The researchers constantly monitored progress for the time trial and completion time was recorded. The participant had no knowledge of their completion time or HR during the time trial so as not to influence performance at subsequent visits. The researchers administered the mouth rinse solutions during the time trial. Subjects were instructed to rinse the solution (25 mL) in their mouth, swishing it around for 5 seconds, which was timed and communicated by researchers. The subjects then expectorated the solution so that none of the solution is swallowed. The amount of expectorated solution was examined by researchers to ensure that none of the solution was swallowed. This rinsing and swishing protocol was incorporated at the following time points: immediately before starting the time trial and every 12.5% of the 12.8 km time trial completed (calculated based on distance covered). The subjects rinsed with the solution a total of 8 times during each time trial.

There was no interaction between the subjects and the researcher other than giving the mouth rinse every 12.5% of the time trial completed and informing the subject of the distance covered and how much is left to complete the 12.8 km time trial. Subjects were also asked to rate their perceived exertion (RPE) based on the Borg scale at the beginning, end, and every 12.5% of the time trial. Following the time trial, HR data was recorded from the heart rate watches, which were programmed to record heart rate at the beginning, end, and every 1-minute during the time trial (Polar Electro, Finland).

Statistical Analysis

Descriptive statistics including mean, range, standard deviation, standard error, and percent change (difference) from control were calculated for all outcome variables. A two-way repeated measures ANOVA was used to determine if there are significant treatment effects on the time trial performance, HR, and RPE for each mouth rinse. If a significant treatment or time effect was found, post hoc analyses were done using a Tukey's test. Statistical significance was set at $p<0.05$.

The experimental protocol was an event-related interleaved design using the same four stimulus conditions (exact same solutions) as was used for the mouth rinsing protocol in a 2.5 ml bolus. Each stimuli, as well as a tasteless rinse solution (25mM KCL+2.5 mM $NaCO_3$) were delivered to the subjects mouth during scanning through four polyethylene tubes held together with a foam mouthpiece containing teeth rivets to secure the apparatus in place and ensure little movement from the head and jaw. Each tube was 5 feet in length and was connected to a separate reservoir via a syringe and a one-way syringe valve operated by the investigators (Fisher Scientific, UK).

Image Acquisition

A 3T Siemens MR system (Skyra, Germany) at the Texas Tech Neuroimaging Institute was used for the fMRI portion of the study. A high resolution T1-weighted anatomical image (FOV: 256 mm axial, voxel dimensions 1.0×1.0×1.0 mm) was acquired for each participant. Blood-oxygen-level dependent (BOLD) contrast images were acquired using a T2*-weighted single-shot echo planar sequence (TR=3000 ms, 3.0×3.0×3.0 mm isotropic voxels, 35 oblique axial slices with a 1 mm gap). One functional scan was performed prior to the solution administration protocol.

Scanning Procedures

Once the subject was fit comfortably in the fMRT, the scanner began, and the subject was prompted in a sequence of events by utilizing EPrime-2 (Psychology Software Tools, Inc, PA) (FIG. 1). The subject was first prompted that the solution would be administered shortly (3 seconds) and when an image of a syringe appeared, the investigator administered the first randomly chosen solution. When the solution reached the oral cavity, the subject was instructed to move their tongue from side to side 1x to ensure distribution of the liquid in the oral cavity. The subject then held the solution in their mouth for 30 seconds and was prompted again when to swallow the solution. A series of 5 questions was then asked following each solution in which the subject rated each solution based on sweetness, bitterness, saltiness, palatability, and intensity. These characteristics were rated with a two button finger toggle using 7-point Likert scale while being scanned. The subject was given 7 seconds to answer each question with a 2 second delay between each question. After answering all questions the subject was then prompted (verbally) that a rinse solution would be administered (tasteless solution described above). This solution was moved around the oral cavity for 5 seconds and swallowed. The subject was then prompted to be prepared for delivery of the next solution. Each subject participated in 2 rounds of the proposed sequencing so that each subject was exposed to each of the five solutions a total of two times.

Image Analysis

Echo planar images were analyzed using FMRIB's (Oxford Centre for fMRI of the Brain) Software Library (FSL; FMRIB, Oxford, UK, http://www.fmrib.ox.ac.uk/fsl). Data processing was carried out using FEAT (FMRI Expert Analysis Tool) version 5.98. At the individual level of analysis, images were motion corrected and realigned (Jenkinson, Bannister, Brady, & Smith, 2002). BOLD signals were spatially smoothed (FWHM=5 mm). FILM (FMRIB's Improved Linear Model) was used to carry out statistical analysis at the level of the individual subject (Woolrich, Ripley, Brady, & Smith, 2001). Custom input files were created to model two randomized rounds of exposure to each solution in each analysis (the introduction of sugar (S), xylitol (X), sucralose (SL) or control (C) into the mouth) convolved with a gamma-shaped haemodynamic response function. Six contrasts were specified to assess the effects of the test solutions above the C solution and between each other (S>C, X>C, SL>C, S>X, S>SL, and X>SL). Functional images were registered to the participant's corresponding extracted T1-weighted image and spatially normalised into a standard space using the Montreal Neurological Institute (MNI) template brain (MNI 152 T1 1 mm brain).

The analyzed contrasts between the solutions were sucrose>control, xylitol >control, sucralose>control, sucrose>xylitol, sucrose>sucralose, and xylitol>sucralose. A fixed effects model was used to perform a group analysis of the lower-level contrast images. An additional random effects analysis (FSL/FEAT FLAME 1+2) did not produce substantially different results. Computed statistic images were thresholded using clusters determined by Z>2.3 and a corrected cluster significance threshold of Puncorrected=0.05. The Harvard-Oxford cortical structural atlas was used to determine the probable location of each significant activation cluster. Thresholded Z-statistic images generated from the higher-level group analysis were overlaid on the MNI template brain in stereotaxic space using MRIcroGL software and images were created for presentation.

Results:

Time Trial

Figure 2:
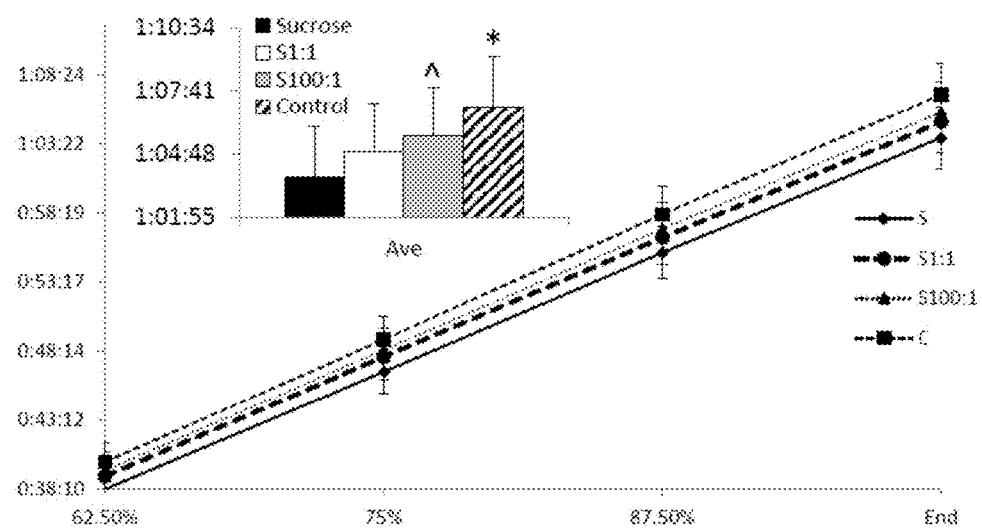
FIG. 2 shows performance times for the final 4 stages (12.5% intervals) of the time trial. Bar graph represents the average completion time for all subjects for all solutions. There was a main effect of treatment (p=0.03) and time (p=0.04) but no treatment x time interaction (p=ns). The S was completed significantly faster than C (p<0.001), and also showed a trend for being faster than S100:1 (p=0.07). No other differences were found. Data presented as mean±SEM. (S=sucrose, 51:1=sucralose 1:1, S100:1=sucralose 100:1, and C=control). *denotes significance vs. S. ^denotes a trend vs. S
Figure 3:
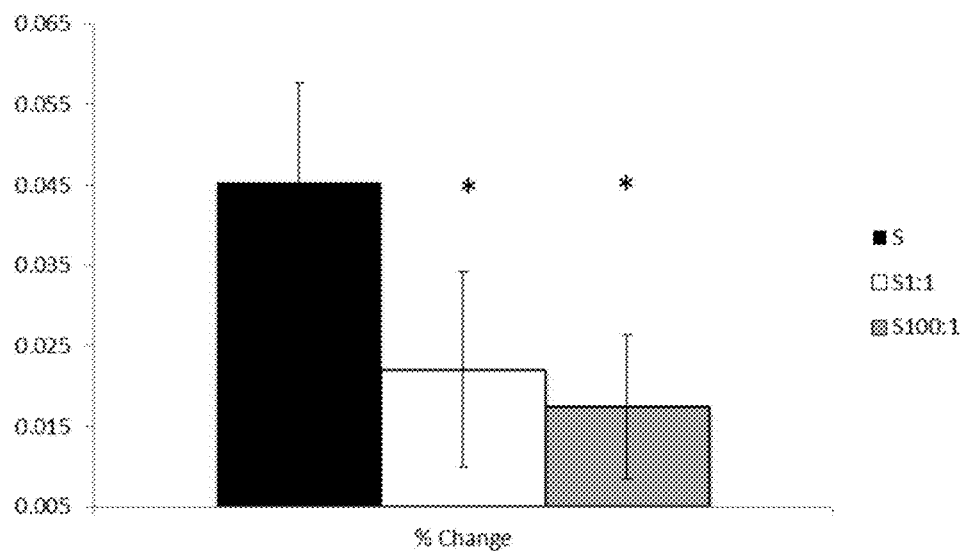
FIG. 3 shows percent change from control (each subject's trial of interest—control/control) revealed that the S time trial was significantly faster than S1:1 (p=0.04) and the S100:1 solution (p=0.01). Data presented as mean±SEM. (S=sucrose, S1:1=sucralose 1:1, S100:1=sucralose 100:1, and C=control) *denotes significance vs. S.

Twenty-one subjects (12 males, and 9 females) completed all four exercise time trials. Descriptive characteristics can be found in Table 1. The mean age and BMI between men and women were not different; while height, weight, and body fat were all different, as expected. The average completion time for all subjects was 63.47±2.17 min for S, 64.55±2.45 min for S1:1, 65.38±2.12 min for S100:1, and 66.56±2.18 min for C (FIG. 2). There was a main effect of treatment (p=0.03) and time (p=0.04) but no treatment x time interaction (p=ns). The S time trial was completed significantly faster than C (p<0.001), and there was a trend for a faster completion time compared to the S100:1 trial (p=0.07). No other treatment differences were found (FIG. 2). When analyzed by gender, as expected, men completed each time trial faster than the women (59.34±3.17 min vs. 69.24±1.26 min for S, 60.14±2.45 min vs. 71.1±3.24 min for S1:1, 60.27±2.34 min vs. 72.34±2.25 min for S100:1, and 61.46±2.41 min vs. 73.5±2.47 min for C, p<0.01) for men vs. women, respectively. However, there were no differences in completion times between solutions when analyzed by gender, so we grouped the genders together for analysis. Finally, analyzing the time trial data based on percent change from control (each subject's trial of interest–control/control) revealed that the S time trial was significantly faster than S1:1 (0.045±0.02 vs. 0.022±0.01, p=0.04) and the S100:1 solution (0.045±0.02 vs. 0.017±0.01, p=0.01) (FIG. 3).

TABLE 1

Subject Characteristics

|  | Men (n = 12) | Women (n = 9) |
| --- | --- | --- |
| Age (yrs) | 25 ± 6.7 | 24 ± 3.0 |
| Height (cm) | 181.3 ± 3.5* | 153.7 ± 2.2 |
| Weight (kg) | 74.7 ± 4.5* | 51.7 ± 2.0 |
| Body Fat % | 10.2 ± 4.1* | 21.1 ± 4.2 |
| BMI (kg/m2) | 21.3 ± 1.2 | 22.0 ± 1.7 |

*denotes significant difference between genders
BMI = Body Mass index

Heart Rate (HR)

Figure 4:
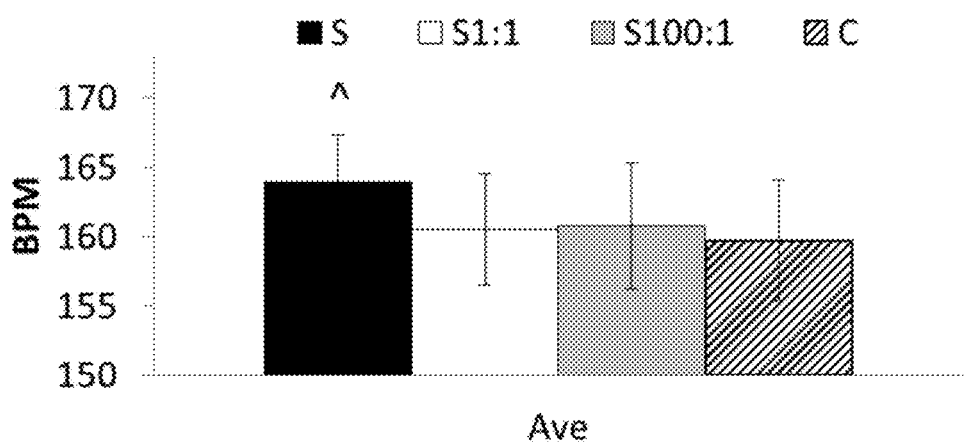
FIG. 4 shows average HR for all subjects for all solutions (S=sucrose, S1:1=sucralose 1:1, S100:1=sucralose 100:1, and C=control). There was a main effect of treatment (p=0.05). The S solution showed a trend for higher average HR compared to C (p=0.08). No other differences between solutions was found. Data presented as mean±SEM. (S=sucrose, S1:1=sucralose 1:1, S100:1=sucralose 100:1, and C=control). ^denotes a trend vs. C.

The average HR across the time trial for each solution is shown in FIG. 4. There was a main effect of treatment (p=0.05). Average HR for S showed a trend for being higher (p=0.08) than the C solution (164.4±2.5 vs. 159.7±2.8bpm for S vs. C, respectively, p=0.08). No other treatment differences for average HR were found. Finally, there were no differences in max HR or percent change from C.

Ratings of Perceived Exertion (RPE)

Figure 5:
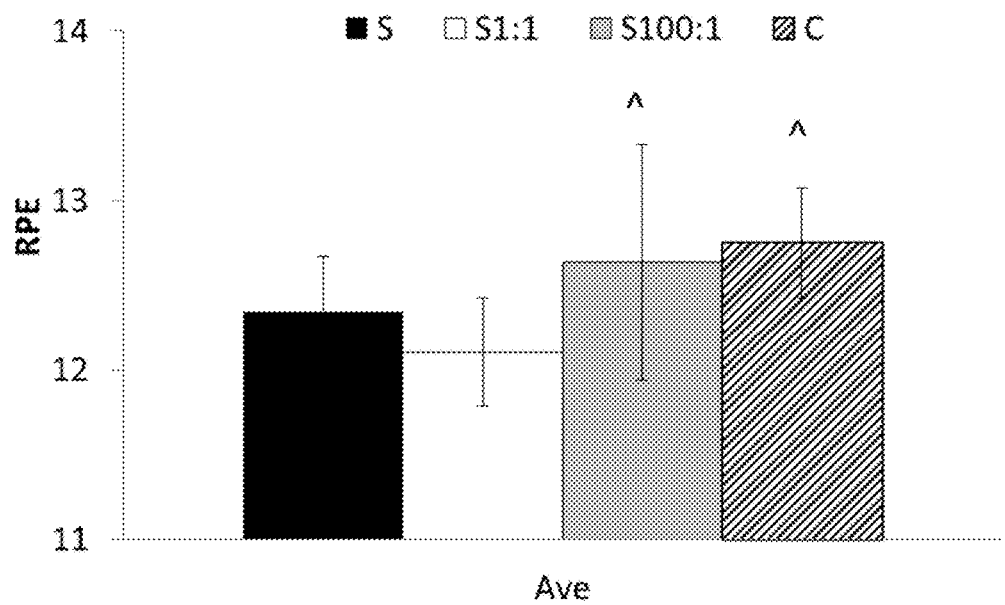
FIG. 5 shows average RPE for all subjects for all solutions. There were no significant differences in RPE shown for any of the solutions. Data presented as mean±SEM. (S=sucrose, S1:1=sucralose 1:1, S100:1=sucralose 100:1, and C=control). ^denotes a trend vs. S1:1.
Figure 6:
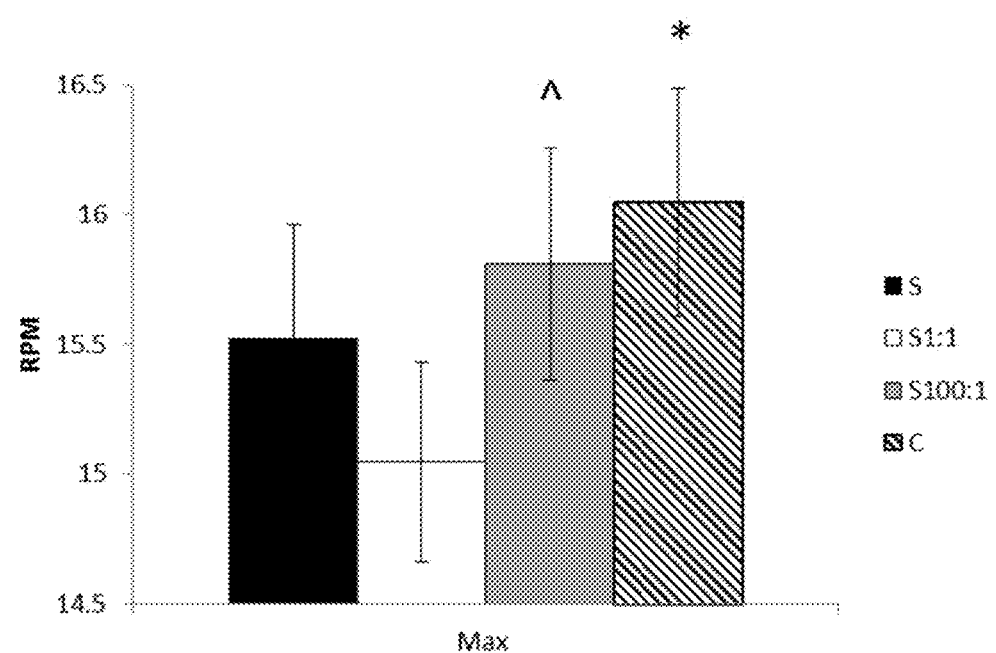
FIG. 6 shows max RPE for all subjects for all solutions. There was a main effect of treatment (p=0.04) for RPE between the solutions. The S1:1 time trial had a lower max RPE than the C (p=0.02) and showed a trend for being lower than S100:1 (p=0.10). No other differences were found. Data presented as mean±SEM. (S=sucrose, S1:1=sucralose 1:1, S100:1=sucralose 100:1, and C=control). *denotes significance vs. S1:1. ^denotes a trend vs. S1:1

Average RPE across the whole time trial for each solution is shown in FIG. 5. There were no significant main effects for RPE for any solution. Additionally, the max RPE for all subjects can be found in FIG. 6. There was a main effect of treatment (p=0.04) for RPE between the solutions. Max RPE was significantly lower for the S1:1 solution vs. control (15.05±0.39 vs. 16.05±0.44, p=0.02) and showed a trend for being lower than S100:1 (15.05±0.39 vs 15.81±0.45, p=0.10).

Neural Activation to Mouthrinse solutions:

The data was analyzed based on significant activation between the solutions based on all subjects (n=17) as well as NW (7) only and OB only (10). The human primary taste cortex, within the gustatory cortex, has been previously shown to be associated with the insular cortex as well as the frontal opercular cortex. These areas are known to be responsible for taste recognition and further processing leading to reward related areas of the brain responsible for recognition of nutritive value. This is known to occur in the secondary taste cortex for humans and includes the orbitofrontal cortex. This area is primarily responsible for reward activation in response to food tastants. For this reason, we chose to focus on the insula, frontal operculum (FO), and the orbitofrontal cortex (OFC) as regions of interest (ROI) to assess primary and secondary taste activation (Table 2).

Primary Taste Cortex ROI:

Each of the sweetened solutions were compared (sucrose, sucralose 1:1 (Si), and sucralose 100:1 (S100) to the control of water). The comparison of sucrose>control, Si>control, and S100>control was performed and activation in the insula for both rounds of exposure to the solutions was observed. Activation in the frontal operculum was significant only for S1>control in round two, but not in sucrose>control or S100>control.

Next, significant activation between all of the sweetened solutions was analyzed (sucrose>S1, sucrose>S100, and Si>S100). For the comparison of sucrose>S1, significant activation within the frontal operculum and the insula in the first and second round of exposure to the solutions, not the second round of exposure in either ROIs, was observed. Sucrose>S100 revealed significantly activated coordinates within the insula, but not the FO in both rounds of exposure. Finally, S1>S100 significantly activated only the FO in round two of exposure with no activation in the insula in either round.

Secondary Taste Cortex ROI:

For the comparison of sucrose>control, S1>control, and S100>control activation in the orbitofrontal cortex was observed in both rounds of exposure to the solutions. Next, significant activation between all of the sweetened solutions was analyzed (sucrose>S1, sucrose>S100, and S1>S100). For the comparison of sucrose>S1, Sucrose>S100, and S1>S100 significant activation within orbitofrontal cortex was observed in both rounds of exposure to the solutions.

TABLE 2

Activation in Regions of Interest (ROI) Associated with Oral Exposure to Mouthrinse Solutions for All subjects (n = 21)

| | Z-stat | Cluster | X | Y | Z | Brain Region |
|---|---|---|---|---|---|---|
| | | | Sucrose > Control | | | |
| R1 | 3.78 | 553 | −38 | −2 | −5 | Insular Cortex |
| | 2.95 | 22 | 23 | 30 | −26 | Frontal Orbital Cortex |
| R2 | 2.58 | 28 | 34 | −18 | 3 | Insular Cortex |
| | 3.17 | 266 | −17 | 10 | −16 | Frontal Orbital Cortex |
| | 2.58 | 49 | 21 | 29 | −8 | Frontal Orbital Cortex |
| | 2.54 | 83 | 26 | 8 | −21 | Frontal Orbital Cortex |
| | 2.52 | 55 | −22 | 14 | −24 | Frontal Orbital Cortex |
| | | | Xylitol > Control | | | |
| R1 | 2.47 | 32 | −36 | −3 | −5 | Insular Cortex |
| R2 | 2.43 | 23 | 33 | 12 | −18 | Insular Cortex |
| | 2.43 | 17 | −33 | 25 | 12 | Frontal Operculum Cortex |
| | 3.01 | 38 | 29 | 29 | −18 | Frontal Orbital Cortex |
| | 2.9 | 25 | −46 | 25 | −16 | Frontal Orbital Cortex |
| | 2.43 | 14 | 17 | 20 | −22 | Frontal Orbital Cortex |
| | 2.41 | 21 | 30 | 21 | −19 | Frontal Orbital Cortex |
| | | | Sucralose > Control | | | |
| R1 | 2.52 | 30 | −36 | −3 | −4 | Insular Cortex |
| | 3.14 | 222 | −27 | 28 | −10 | Frontal Orbital Cortex |
| | 2.53 | 79 | −32 | 36 | −8 | Frontal Orbital Cortex |
| R2 | 2.5 | 78 | 41 | −6 | 7 | Insular Cortex |
| | 2.49 | 18 | 33 | 21 | −4 | Insular Cortex |
| | 3.12 | 66 | 22 | 16 | −17 | Frontal Orbital Cortex |
| | 3.07 | 56 | −15 | 7 | −26 | Frontal Orbital Cortex |
| | 2.49 | 30 | 20 | 34 | −16 | Frontal Orbital Cortex |
| | | | Sucrose > Xylitol | | | |
| R1 | 2.44 | 63 | 43 | −12 | 9 | Insular Cortex |
| | 3.61 | 452 | 36 | 25 | 14 | Frontal Operculum Cortex |
| | 3.05 | 311 | −37 | 16 | 16 | Frontal Operculum Cortex |
| | 2.47 | 88 | 41 | 12 | 13 | Frontal Operculum Cortex |
| | 2.44 | 21 | 17 | 19 | −21 | Frontal Orbital Cortex |
| R2 | 2.47 | 48 | 25 | 8 | −21 | Frontal Orbital Cortex |
| | | | Sucrose > Sucralose | | | |
| R1 | 3.59 | 377 | 44 | −4 | 1 | Insular Cortex |
| | 3.16 | 85 | −38 | −18 | 15 | Insular Cortex |
| | 2.72 | 24 | −39 | −5 | −5 | Insular Cortex |
| | 3.53 | 88 | 22 | 28 | −25 | Frontal Orbital Cortex |
| R2 | 2.76 | 40 | 32 | 6 | −11 | Insular Cortex |
| | 3.17 | 79 | −28 | 24 | −11 | Frontal Orbital Cortex |
| | 2.31 | 21 | 23 | 31 | −7 | Frontal Orbital Cortex |
| | | | Xylitol > Sucralose | | | |
| R1 | 3.23 | 76 | 28 | 28 | −28 | Frontal Orbital Cortex |
| | 2.42 | 17 | −23 | 34 | −7 | Frontal Orbital Cortex |
| | 2.35 | 26 | 31 | 28 | −4 | Frontal Orbital Cortex |

Discussion:

The purpose of this study was to investigate the effects of utilizing sweetened mouth rinses, which contain differing energy content and sweet taste intensity, during a 12.8 km time trial. Further, central responses were investigated using fMRI to detect the magnitude of change in blood oxygen level dependent (BOLD) signal in response to receipt of each mouth rinse (sucrose, xylitol, sucralose, and water). Energy availability in the mouth rinses was required for observed improvements in exercise performance and sweet taste alone was not enough to improve performance compared to water. Although the existence of the physiological responses to sweet taste has been shown in the past, the central and peripheral effects of these responses in humans are still not fully understood. The results of this study indicate that carbohydrate mouthrinse is an effective strategy for improving exercise performance; but the presence of energy content seems to be the key mechanism due to associations with reward-value driven processes in the brain.

The sucrose solution decreased performance time when compared to the control solution of water, but had no effect on HR or RPE. The S1 and S100 solutions did not improve exercise performance measures when compared to water, and when the ergogenic effect was examined between the sweetened mouthrinses, neither were significantly different from one another. Interestingly, there was a trend for the sucrose solution resulting in a quicker time trial performance than the sucralose solution. This may be due to the intensity of sweetness in the S100 solution. There is a sweet taste threshold in humans and beyond a specific intensity, which varies greatly among individuals, the taste becomes aversive.

Sweet taste perception can trigger the brain reward system for measures of taste quality as well as an incentive motivational component (Bartoshuk L M, et al. Philos Trans R Soc Lond B Biol Sci. 2006 361:1137-48; Connolly L, et al. Neurogastroenterol Motil. 2013 25(7):579-e460; Yang Q. Yale J Biol Med. 2010 83:101-8; Berthoud H R. Curr Opin Neurobiol. 2011 21:888-96; Berthoud H R. Physiol Behav. 2005 85:1-2; Berthoud H R. Appetite. 2004 43:315-7; Lenard N R, et al. Obesity (Silver Spring). 2008 16 Suppl 3:S11-S22; Zheng H, et al. Physiology (Bethesda). 2008 23:75-83). Neural response comparing energy content and intensity of sweet taste between the sweetened solutions revealed activation in all three ROIs. Sucrose also activated the insula as well as the orbitofrontal cortex but not the frontal operculum when compared to the higher intensity S100 solution. A comparison between the two solutions that only contain sweet taste and no energy reveals activation in the insula, but not in the other two ROIs. The findings confirm that sucrose, which contains energy and sweet taste, activates taste recognition and reward related regions of the brain differently than sucralose, which contains only sweet taste (Frank G K, et al. Neuroimage. 2008 39:1559-69). The neural activation patterns seen here indicate that detection of sensory cues are highly variable among individuals and variability in a central response should be considered when evaluating the effectiveness of mouth rinsing solutions with the goal of reducing fatigue. Neural communication dedicated to relaying information for the nutritive value of food separate from the sweet taste of food may have evolved as a separate part of a homeostatic system that responds to the consumption of highly nutritive foods or when rates of fuel depletion are rapid or when fuel reserves are limited. The sensory system is most likely responsible for the detection of energy dense nutrients which can encode sweet taste separately from nutritive value. Activation of taste recognition areas of the brain as well as processing of reward value are more intense when in a fasted vs. a fed state.

Sensory detection is the first stage of proper energy utilization and highly imperative for efficient communication of incoming substances as well as proper subsequent metabolic responses leading to efficient utilization of energy stores. The potential of intensity of sweet taste to influence exercise performance results from an innate hypersensitivity to sweet taste and in most mammals, including humans, sweet receptors evolved in ancestral environments with reduced sugar availability and therefore are not adapted to high products containing high amounts of sugar (Berthoud H R. Physiol Behav. 2007 91:486-98; Small D M. Brain Struct Funct. 2010 214:551-61). When taste receptors come in contact with substances that produce a greater sensory response than would normally be expected, the brain reward signal is also increased. This observation is paralleled with the capacity to override mechanisms related to self-control and motivation (Berthoud H R. Curr Opin Neurobiol. 2011

21:888-96; Berthoud H R. Appetite. 2004 43:315-7; Berthoud H R. Obesity (Silver Spring). 2006 14 Suppl 5:197S-200S). In the case of central fatigue during exercise, the intensity of sweet taste could signal an incoming source of energy in a time when the metabolic processes are especially vulnerable, although as shown here, energy content does seem to be the most important impact factor for effective utilization of mouth rinses to improve exercise measures.

Hormones released in response to cephalic phase reflexes are thought to be dependent on neural rather than nutrient-induced stimulation and these hormone responses could have implication in the responsivity of individuals to mouth rinsing for improved performance (Berthoud H R. Curr Opin Neurobiol. 2011 21:888-96; Berthoud H R. Physiol Behav. 2007 91:486-98; Shin A C, et al. Physiol Behav. 2009 97:572-80). Each hormone in the islet of langerhans displays a different sensitivity to inhibition and stimulation by both the sympathetic nervous system (SNS) as well as the parasympathetic nervous system (PNS), so different profiles of hormonal release can occur in response to oral sensory stimulation (Henquin J C. Sci Signal. 2012 5:e36; Kojima I, et al. Diabetes Metab J. 2011 35:451-7). Further, importance has been placed on the role of variability in physiological responses due to individual taste recognition responsiveness and that proper response from all aspects of this dynamic system are essential for overall homeostasis. Sensory response to flavor has been known to activate other physiological functions such as thermogenesis and metabolic effects which can include an early phase insulin release, changes in blood glucose levels, respiratory quotient, plasma free fatty acid levels, and hepatic enzyme activity (Teff K. Appetite. 2000 34:206-13; LeBlanc J. Appetite. 2000 34:214-6; Parra-Covarrubias A, et al. Diabetes. 1971 20:800-2). The associated physiological response to mouthrinsing during exercise could impact exercise response.

CONCLUSION

The findings of this study show that mouth rinsing sweet tasting solutions was shown to be associated with improvements in physical performance compared to an unsweetened control. There seems to be an increased effectiveness of using this method when energy content is present in the solution as opposed to sweet taste alone. Activation in areas of the brain involved in taste recognition and reward and motivation were intensified to the greatest extent by sucrose, mostly likely due to the presence of energy as well as sweet taste. These results highlight the proposal that there is a possible neural mechanism committed to detecting energy value separately from sweet taste which seems to be more effective during times of energy deprivation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for enhancing exercise performance in a subject, comprising contacting the oral cavity of the subject with a composition comprising a sweet and caloric food product for a period of 5 seconds to 60 seconds without ingestion of the food product, wherein the oral cavity of the subject is contacted with the composition after fasting intervals of at least 6 to 10 minutes.

2. The method of claim 1, wherein the food product comprises a sugar.

3. The method of claim 2, wherein the sugar comprises sucrose.

4. The method of claim 1, wherein the food product contains calories and has a sweetness equivalent to at least 5 wt % sucrose.

5. The method of claim 1, wherein the oral cavity is first contacted with the composition during the last 20 minutes of the exercise.

6. The method of claim 1, wherein the composition is in the form of a tablet, capsule, lozenge, film, or strip that can completely dissolve in the oral cavity of a human subject within 60 seconds.

7. The method of claim 1, wherein the composition is in the form of an orally consumable film or strip, wherein the film or strip completely dissolves in the oral cavity within 60 seconds.

8. The method of claim 7, wherein the film or strip comprises a mucoadhesive polymer.

9. The method of claim 2, wherein the sugar comprises glucose.

* * * * *